United States Patent
Kimball et al.

(10) Patent No.: US 7,845,055 B1
(45) Date of Patent: Dec. 7, 2010

(54) TAMPON FORMED FROM A SELECTIVELY NEEDLED NONWOVEN FABRIC WEB

(75) Inventors: David L. Kimball, Flemington, NJ (US); Anthony C. Lalama, North Brunswick, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 12/608,174

(22) Filed: Oct. 29, 2009

(51) Int. Cl.
  *D04H 1/22* (2006.01)
  *D04H 18/00* (2006.01)
  *A61F 13/22* (2006.01)

(52) U.S. Cl. .................. 28/118; 28/107; 28/110; 28/112

(58) Field of Classification Search .......... 28/118, 28/107, 109, 110, 111, 112, 113–115, 119, 28/120, 122, 123; 604/385.17, 385.18, 904
See application file for complete search history.

(56) References Cited

U.S. PATENT DOCUMENTS

| | | | |
|---|---|---|---|
| 2,566,190 A * | 8/1951 | Greiner et al. | 28/118 |
| 2,902,746 A | 9/1959 | Bateman | |
| 3,199,166 A | 8/1965 | Petersik | |
| 3,368,256 A | 2/1968 | Fehrer et al. | |
| 3,422,496 A | 1/1969 | Justus et al. | |
| 3,606,643 A * | 9/1971 | Mooney | 28/119 |
| 3,695,270 A * | 10/1972 | Dostal | 604/375 |
| 3,811,445 A * | 5/1974 | Dostal | 604/375 |
| 4,187,586 A * | 2/1980 | Semjonow | 19/161.1 |
| 4,816,100 A | 3/1989 | Friese | |
| 4,884,324 A | 12/1989 | Stanislaw | |
| 5,165,152 A * | 11/1992 | Kramer et al. | 28/118 |
| 5,307,546 A | 5/1994 | Dilo | |
| 5,371,928 A | 12/1994 | Dilo | |
| 5,454,145 A | 10/1995 | Wattel et al. | |
| 5,504,979 A | 4/1996 | Sheehan et al. | |
| 5,732,453 A | 3/1998 | Dilo et al. | |
| 5,822,834 A | 10/1998 | Jourde et al. | |
| 5,864,930 A | 2/1999 | Jourde et al. | |
| 5,873,152 A | 2/1999 | Jourde et al. | |
| 5,909,884 A * | 6/1999 | Schwankhart | 28/118 |
| 6,161,269 A | 12/2000 | Dilo | |

(Continued)

FOREIGN PATENT DOCUMENTS

EP          492432 A     7/1992

(Continued)

*Primary Examiner*—Amy B Vanatta

(57) ABSTRACT

A method and apparatus for manufacturing absorbent tampons with reduced fiber fluff includes a novel needlepunching unit. The method includes the steps of providing a continuous nonwoven fibrous web; separating individual nonwoven web sections from the continuous nonwoven fibrous web; forming distinct side edges of each individual nonwoven web section; rolling the nonwoven web section to form a substantially cylindrical tampon blank; and compressing the substantially cylindrical tampon blank to form the absorbent tampon. The distinct side edges of each individual nonwoven web section are formed by needlepunching proximate the longitudinal side edges of each individual nonwoven web section, folding both longitudinal side edges inwardly to form distinct side edges of the individual nonwoven web section, and needlepunching the folded longitudinal side edges to stabilize the distinct side edges of the individual nonwoven web section. The nonwoven web section is rolled about a winding axis substantially parallel to the width to form the substantially cylindrical tampon blank having an insertion end and a withdrawal end.

13 Claims, 3 Drawing Sheets

U.S. PATENT DOCUMENTS

| | | |
|---|---|---|
| 6,270,486 B1 | 8/2001 | Brown et al. |
| 6,310,269 B1 | 10/2001 | Friese et al. |
| 6,635,799 B1 | 10/2003 | Osborn, III et al. |
| 6,743,212 B1 | 6/2004 | Cole et al. |
| 7,628,114 B2 * | 12/2009 | Aoyama et al. ........ 112/475.08 |
| 2003/0105444 A1 * | 6/2003 | Lochte et al. ................ 604/370 |
| 2005/0281976 A1 | 12/2005 | Curro et al. |
| 2006/0048356 A1 | 3/2006 | Leger |
| 2006/0288548 A1 | 12/2006 | Jean et al. |
| 2008/0124993 A1 * | 5/2008 | Brady ........................ 442/142 |

FOREIGN PATENT DOCUMENTS

| | | | |
|---|---|---|---|
| EP | 520869 | A | 12/1992 |
| EP | 531680 | A | 3/1993 |
| EP | 679379 | A | 11/1995 |
| EP | 786027 | B | 7/1997 |
| EP | 892102 | A | 1/1999 |
| EP | 1056423 | B | 12/2000 |
| EP | 1132513 | A | 9/2001 |
| GB | 1414988 | A | 11/1975 |
| WO | WO 96/11294 | A | 4/1996 |
| WO | WO 99/32061 | A | 1/1999 |
| WO | WO 02/13750 | A | 2/2002 |
| WO | WO 2007/087577 | A | 10/2008 |

* cited by examiner

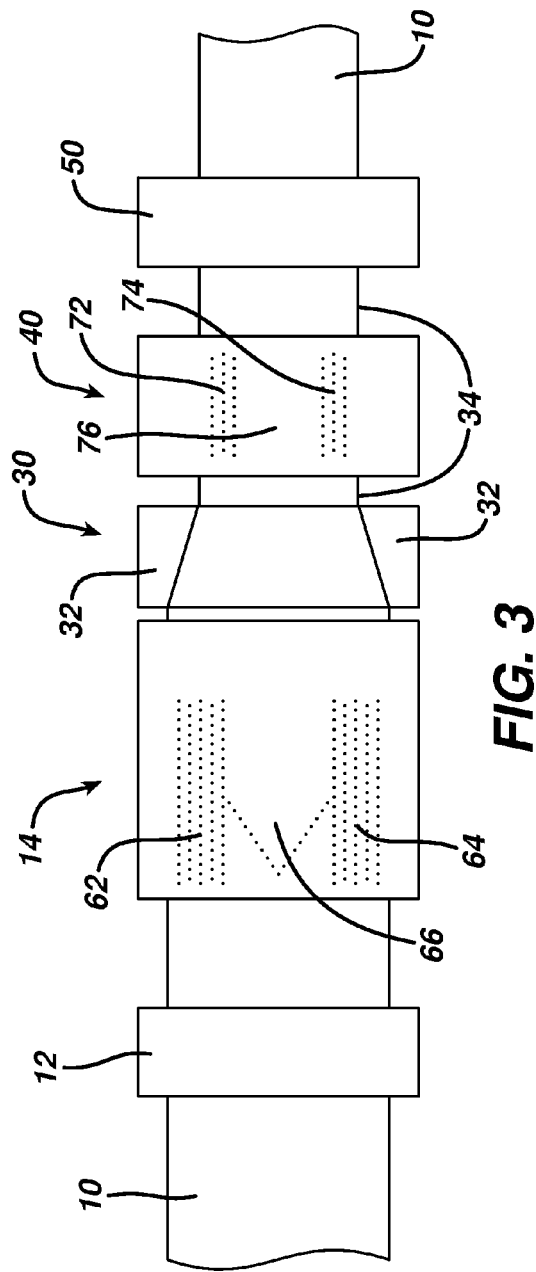
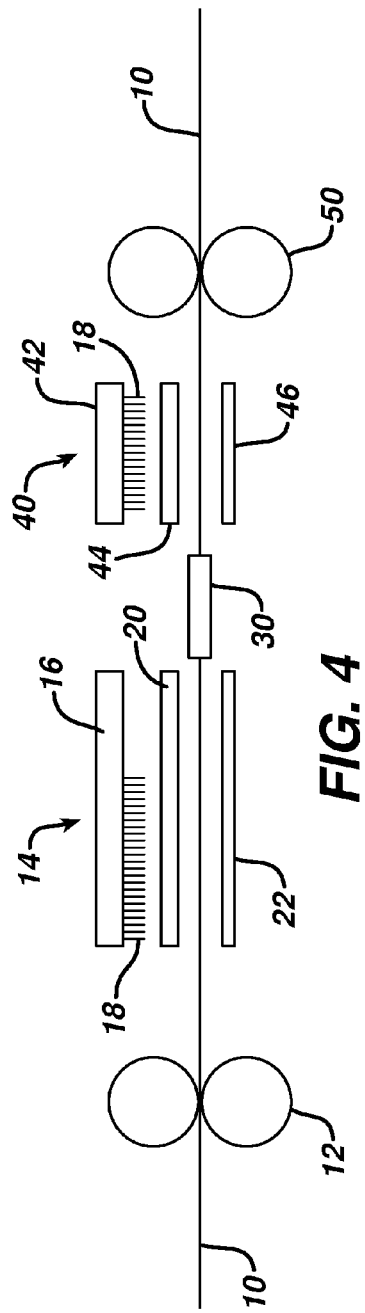
FIG. 3
FIG. 4

TAMPON FORMED FROM A SELECTIVELY NEEDLED NONWOVEN FABRIC WEB

BACKGROUND OF THE INVENTION

The present invention relates to a method of manufacturing tampons employing a needling apparatus. In particular, the method and apparatus is useful in the manufacture of absorbent tampons for feminine hygiene.

Various methods of manufacturing absorbent tampons are known. One relatively well-known method is used to manufacture commercial, radially-expanding tampons. The method is generally disclosed in U.S. Pat. No. 3,422,496, U.S. Pat. No. 4,816,100, and U.S. Pat. No. 6,310,269. In this method, a portion of length of nonwoven material is wound up to form an approximately cylindrical blank of fibrous material. The circumferential surface of this cylindrical blank is pressed radially relative to the longitudinal mid-axis of the cylindrical blank. The nonwoven material may be provided to this process through several methods. Generally, the nonwoven is formed of a carded fibrous web that is gathered to form a narrow strip of the fibrous material. As the side edges of this strip ultimately form the insertion and withdrawal ends of the resulting tampon, the condition of the edges of the strip influence the quality of the final tampon product.

Various methods of forming nonwoven fabrics are known, including needlepunching. In such a method, loose fibers are interlocked into a nonwoven structure by use of reciprocating barbed needles through the massed fibers to displace fibers from a generally transverse orientation to a perpendicular orientation. The needled fabric with perpendicularly oriented fibers is substantially stronger than the massed fiber structure prior to needling. Examples of needlepunching apparatus and methods are disclosed in EP 492-432, EP 520869, EP 1983930, U.S. Pat. No. 2,036,766, U.S. Pat. No. 2,902,746, and U.S. Pat. No. 3,199,166.

These apparatus and methods generally provide large nonwoven fabric webs that are subsequently slit and rolled for storage prior to subsequent use in other manufacturing operations. The slitting is critical to provide neat and clean edges of the fabric webs. Otherwise, uneven edges allows for fibers to extend from these edges resulting in unsightly fiber extensions from the resulting product. Worse yet, these fiber extensions can become loose from the fabric web. The slitting operations thus provide for clean fabric web edges. We have discovered that employing a small needling apparatus in the manufacture of individual fibrous tampons without slitting the edges results in the drawbacks described above. Therefore, what is needed is a small, efficient apparatus and method to form nonwoven fabric webs that can be used in the manufacture of absorbent tampons that greatly reduces fiber extensions from the fabric web edges.

SUMMARY OF THE INVENTION

Surprisingly, we have found a novel way to address the problem of fiber extensions or fluff in tampon manufacture. In one aspect of the invention a method of manufacturing absorbent tampons includes the steps of providing a continuous nonwoven fibrous web; separating individual nonwoven web sections from the continuous nonwoven fibrous web; forming distinct side edges of each individual nonwoven web section; rolling the nonwoven web section to form a substantially cylindrical tampon blank; and compressing the substantially cylindrical tampon blank to form the absorbent tampon. Each individual nonwoven web section has a length greater than a width, a thickness substantially less than both the length and width, and longitudinal side edges. The distinct side edges of each individual nonwoven web section are formed by needlepunching proximate the longitudinal side edges of each individual nonwoven web section, folding both longitudinal side edges inwardly to form distinct side edges of the individual nonwoven web section, and needlepunching the folded longitudinal side edges to stabilize the distinct side edges of the individual nonwoven web section. The nonwoven web section is rolled about a winding axis substantially parallel to the width to form the substantially cylindrical tampon blank having an insertion end and a withdrawal end.

In another aspect of the invention, an apparatus for manufacturing absorbent tampons includes an individual nonwoven web section feeder; a needling unit; a transport section; and a tampon former. The needling unit includes first and second needlepunching sections separated by a longitudinal edge folding section. The first needlepunching section has a first region having a first needle density corresponding to a first longitudinal side edge of the individual nonwoven web section and a second region having a second needle density corresponding to a second longitudinal side edge of the individual nonwoven web section. The second needle density may be less than the first needle density. The longitudinal edge folding section is arranged and configured to fold the first and second longitudinal side edges of the individual nonwoven web section inwardly. The second needlepunching section has a third region having a third needle density corresponding to the first longitudinal side edge of the individual nonwoven web section, and a fourth region having a fourth needle density corresponding to the second longitudinal side edge of the individual nonwoven web section. The transport section moves the individual nonwoven web section to a winding section, which winds the individual nonwoven web section about a winding axis generally parallel to the width of the individual nonwoven web section to form a substantially cylindrical tampon blank. The tampon blank has an insertion end defined at least in part by the second longitudinal side edge of the individual nonwoven web section and a withdrawal end defined at least in part by the first longitudinal side edge of the individual nonwoven web section. The transforms the substantially cylindrical tampon blank into the absorbent tampon.

BRIEF DESCRIPTION OF THE DRAWINGS

FIG. 3 is a plan view of one embodiment of the apparatus of the present invention.

FIG. 4 is a side elevation of the apparatus of FIG. 3.

DETAILED DESCRIPTION OF THE PREFERRED EMBODIMENT

Figure 1:
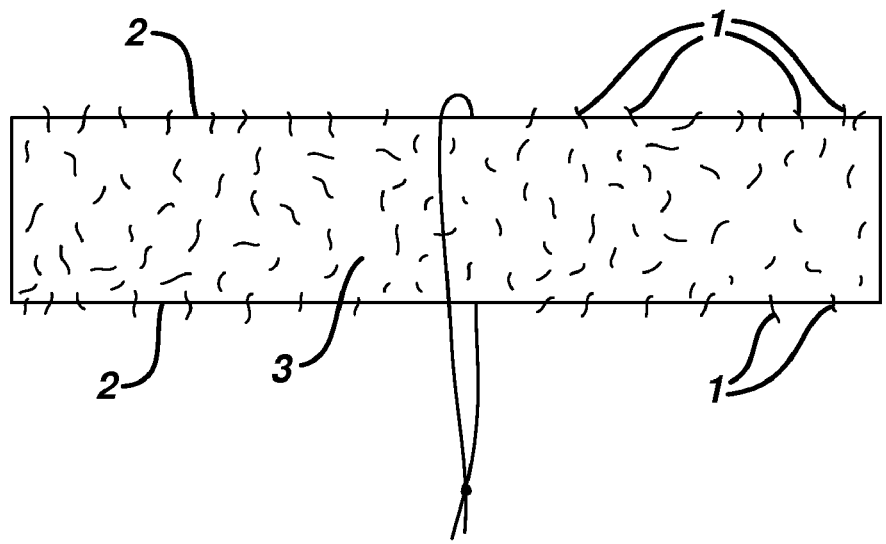
FIG. 1 is a plan view of an individual nonwoven web section of the prior art
Figure 2:
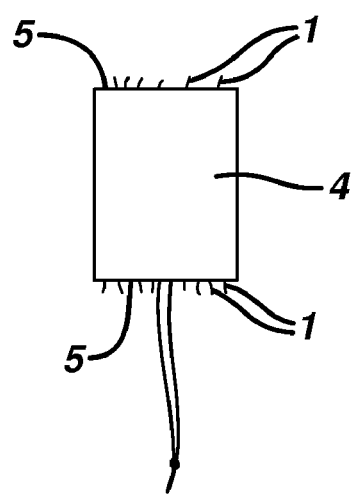
FIG. 2 is a side elevation of a tampon blank of the prior art.

According to a state-of-the-art process for manufacturing tampons, a cohesive absorbent fibrous web is created by (1) carding a blend of absorbent fibers, (2) gathering the carded fibers to form a continuous, narrow web, and (3) calendaring the web into the cohesive web which can be processed in the tampon maker. As shown in FIG. 1, loose fibers 1 can be present at the side edges 2 of the absorbent fibrous web 3. When this material is rolled up to form a tampon blank 4 as described in U.S. Pat. No. 4,816,100, these fibers 1 can extend from the cylindrical ends 5 of the tampon blank 4 as shown in FIG. 2. This can ultimately affect the overall appearance of the resulting tampon as fibrous with "fluff" at the withdrawal end (the end with the withdrawal string 6) and/or at the insertion end.

Such a process can use an apparatus that includes the following devices that may be arranged in series in the direction of processing:
- a supply a continuous nonwoven web of natural and/or synthetic fibers;
- a station for separating individual nonwoven web sections from the supply;
- a cover attachment section;
- a withdrawal string attaching and knotting device;
- a winding station for rolling up the nonwoven web section to form a tampon blank;
- a device for transferring the tampon blank to a press, in which the tampon blank can be pressed substantially radially to give the final form of the tampon,
- a device for forming the introduction end of the tampon, and
- a device for packaging the tampon.

A number of the above process steps may be rearranged without significantly affecting the resulting product. For example, the cover attachment section may be moved to precede or follow either of the withdrawal string attaching and knotting device and the station for separating individual nonwoven web section.

In the present invention, an additional step is provided that forms clean side edges of the nonwoven web. In particular, a needlepunching section forms the clean side edges of the nonwoven web. The needlepunching section includes an entry needling area, a middle edge folding area and an exit needling area. The entry needling area entangles the thickness direction of the web, the folding area folds the side edges of the web to form clean, distinct side edges, and the exit needling area further entangles the thickness dimension of the web, especially by the edges to maintain the clean appearance of the side edges that are substantially clean of free fibers extending outwardly.

FIGS. 3 and 4 show a portion of the tampon manufacturing process and equipment used therein. A continuous nonwoven web 10 is received from a supply. This web 10 may pass through a first calendar 12 to both slightly compress the web and to draw it into a first needling zone 14. The first needling zone 14 includes a first needle board 16, supporting needles 18, a first stripper plate 20, and a first bed plate 22. The needle points are disposed in spaced relation to the board 16. The first stripper plate 20 has perforations positioned so that, upon reciprocation of the first needle board 16, the needles 18 pass through these perforations and through corresponding perforations in the first bed plate 22. As the web 10 passes between the first stripper plate and the first bed plate, barbs disposed near the tip of the needles 18 carry and interlock fibers across the thickness of the web 10. The shape and sized of the barbs affect the resulting needled web, as is known to those of ordinary skill in the art.

The web 10 then passes through a folding station 30 with folding blades 32. The folding blades 32 fold side margins of the web 10 inwardly to present clean side edges 34.

Immediately following the folding station 30, a second needling zone 40 is present to interlock the folds formed in the folding station 30 to maintain the clean side edges 34. The second needling zone 40 includes a second needle board 42, supporting needles 18, a second stripper plate 44, and a second bed plate 46. Again, the second stripper plate 44 and second bed plate 46 have perforations aligned with the needles 18.

Finally, a second calendar 50 may be present to further define the nonwoven absorbent web 10 and to pull the web 10 through the needling zones and toward the tampon forming press.

We have found that the needling process of the present invention affects both the appearance and absorbent properties of the resulting tampon product. In particular, there is a balance between reducing the fiber fluff extending from the ends of the tampon and the ability of the compressed tampon to expand and to absorb fluid. We have also found that the problem of fiber fluff is greatest at the withdrawal end of the tampon, so we have found it desirable to integrate the nonwoven web more along the side edge associated with the withdrawal end of the tampon when employing the general process disclosed in U.S. Pat. No. 3,422,496, U.S. Pat. No. 4,816,100, and U.S. Pat. No. 6,310,269, the disclosures of which are hereby incorporated by reference.

Therefore, as shown in FIG. 3, the needling pattern of the first needling zone 14 has a first region 62 (adjacent a first side edge corresponding to the withdrawal end of the resulting tampon) that has a first needle density and a second region 64 (adjacent the opposite side edge) that has a second needle density. The first needle density is greater than the second needle density, and therefore, the needles are more closely spaced in the first region. A third region 66 is located between the first and second regions, and the needles may be spaced as desired. This third region 66 may not require the needle density of either of the other two regions.

The second needling zone 40 also has regions of differing needle density/characteristics. A first region 72 (adjacent a first side edge corresponding to the withdrawal end of the resulting tampon) that has a first needle density and a second region 74 (adjacent the opposite side edge) that has a second needle density. Again a third region 76 may be located between the first and second regions. This third region 76 may or may not include needles, as desired.

Depending upon the desired outcome, one of ordinary skill will recognize that one may vary the number and location of needling zones, and may vary the number, spacing and type of needle used in the different regions. Indeed, it may be desired to have the needling in each region employ the same needles and needle density and/or spacing, especially the regions adjacent the side edges of the web.

After the needled web passes from the second calendar 50, it may proceed for further processing into a compressed tampon, again, as generally described in U.S. Pat. No. 3,422,496, U.S. Pat. No. 4,816,100, and U.S. Pat. No. 6,310,269.

EXAMPLES

The present invention will be further understood by reference to the following specific Examples that are illustrative of the composition, form and method of producing the device of the present invention. It is to be understood that many variations of composition, form and method of producing the device would be apparent to those skilled in the art. The following Example is only illustrative.

Example 1

Figure 5:
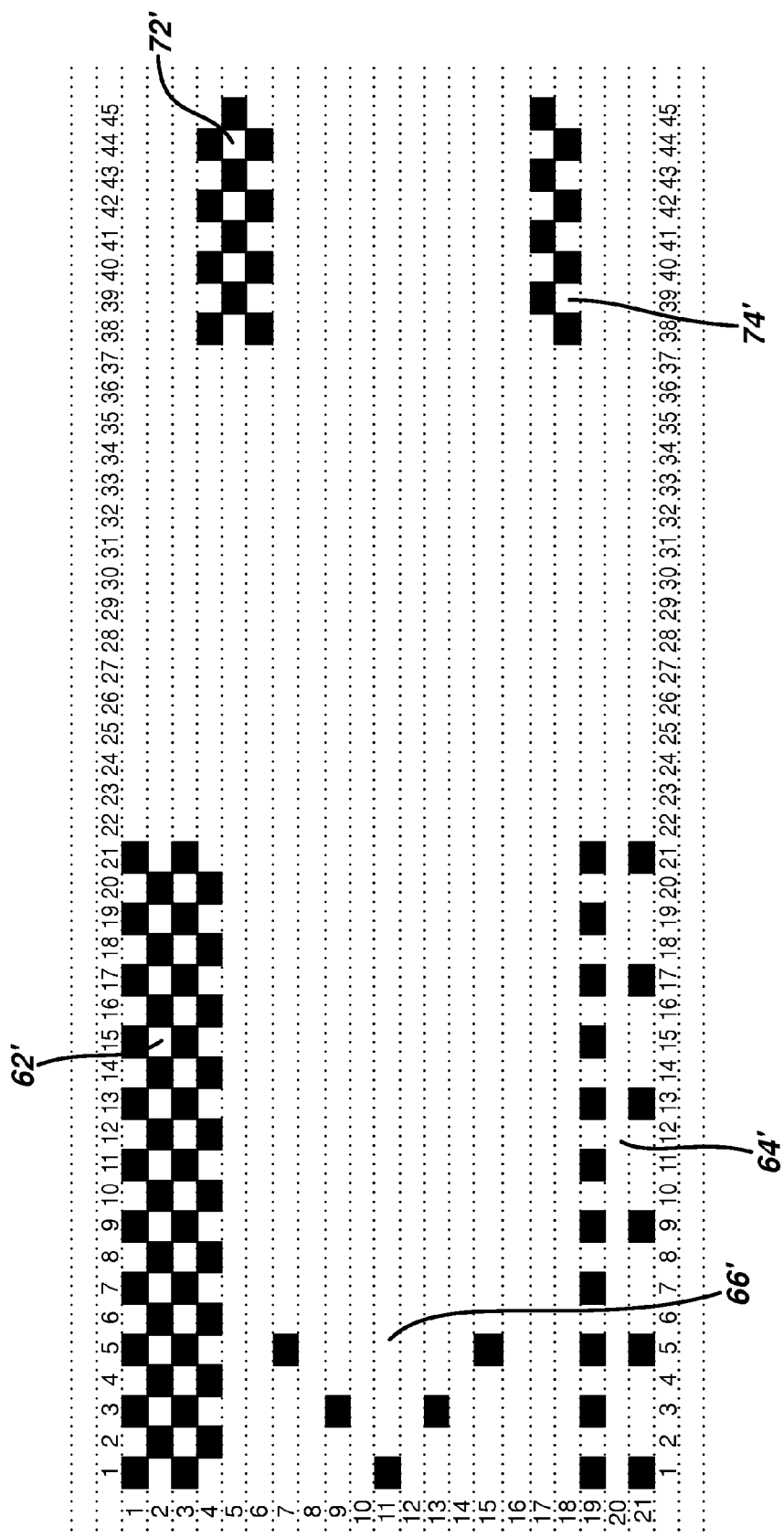
FIG. 5 is a schematic plan of a needle board useful in one embodiment of the present invention.

Tampon webs were formed of a blend of 75 wt-% Galaxy® trilobal viscose rayon fibers available from Kelheim Fibres GmbH Kelheim, Germany and 25 wt-% standard viscose rayon fibers, gathered from a carded web and precalendered as generally described in U.S. Pat. No. 3,422,496, U.S. Pat. No. 4,816,100, and U.S. Pat. No. 6,310,269, and processed according to the present invention. This process employed a needle board with five distinct needling zones (corresponding to regions 62, 64, 66, 72, and 74 in FIG. 3). The relative needle spacing is as shown in FIG. 5, with rows and columns numbered for clarity. The first region 62' includes 42 star blade (sb) felting needles (Foster Needle Co., Inc., Manitowoc, Wis., USA), the second region 64' includes 17 pinch blade (pb) felting needles Foster Needle Co., Inc.), the third region 66' includes 5 pb needles, the first region 72' of the second needling zone includes 12 sb needles, and the second region 74' of the second needling zone includes 8 pb needles. The fibrous web is advanced through the needling section at approximately 75 feet per minute, and the needle board operates at approximately 700 cycles per minute. The resulting web had clean side edges and produced an absorbent tampon with significantly reduced "fluff" and good absorbent characteristics.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method of manufacturing absorbent tampons comprising:
   a. providing a continuous nonwoven fibrous web;
   b. separating individual nonwoven web sections from the continuous nonwoven fibrous web, each individual nonwoven web section having:
      i. a length greater than a width;
      ii. a thickness substantially less than both the length and width; and
      iii. longitudinal side edges;
   c. forming distinct side edges of each individual nonwoven web section by:
      i. needlepunching proximate the longitudinal side edges of each individual nonwoven web section;
      ii. folding both longitudinal side edges inwardly to form distinct side edges of the individual nonwoven web section; and
      iii. needlepunching the folded longitudinal side edges to stabilize the distinct side edges of the individual nonwoven web section;
   d. rolling the nonwoven web section about a winding axis substantially parallel to the width to form a substantially cylindrical tampon blank having an insertion end and a withdrawal end; and
   e. compressing the substantially cylindrical tampon blank to form the absorbent tampon.

2. The method of claim 1, wherein the step of needlepunching proximate the longitudinal side edges of each individual nonwoven web section comprises:
   a. needlepunching a first region adjacent the longitudinal side edge corresponding to the withdrawal end of the substantially cylindrical tampon blank with a first needle density; and
   b. needlepunching a second region adjacent the longitudinal side edge corresponding to the insertion end of the substantially cylindrical tampon blank with a second needle density, less than the first needle density.

3. The method of claim 1, wherein the step of needlepunching the folded longitudinal side edges comprises:
   a. needlepunching a third region adjacent the longitudinal side edge corresponding to the withdrawal end of the substantially cylindrical tampon blank with a third needle density; and
   b. needlepunching a fourth region adjacent the longitudinal side edge corresponding to the insertion end of the substantially cylindrical tampon blank with a fourth needle density.

4. The method of claim 3, wherein the third and fourth needle density are less than the first needle density.

5. The method of claim 1, which further comprises the steps of applying a cover material to the individual nonwoven web sections; providing a withdrawal string; and packaging the absorbent tampon.

6. The method of claim 1, which further comprises the step of calendering the individual nonwoven web sections prior to forming the substantially cylindrical tampon blank.

7. Apparatus for manufacturing absorbent tampons comprising:
   a. an individual nonwoven web section feeder, each individual nonwoven web section having:
      i. a length greater than a width;
      ii. a thickness substantially less than both the length and width; and
      iii. longitudinal side edges;
   b. a first needlepunching section comprising:
      i. a first region having a first needle density corresponding to a first longitudinal side edge of the individual nonwoven web section; and
      ii. a second region having a second needle density corresponding to a second longitudinal side edge of the individual nonwoven web section;
   c. a longitudinal edge folding section arranged and configured to fold the first and second longitudinal side edges of the individual nonwoven web section inwardly;
   d. a second needlepunching section comprising:
      i. a third region having a third needle density corresponding to the first longitudinal side edge of the individual nonwoven web section; and
      ii. a fourth region having a fourth needle density corresponding to the second longitudinal side edge of the individual nonwoven web section;
   e. a transport section to move the individual nonwoven web section to a winding section, the winding section winding the individual nonwoven web section about a winding axis generally parallel to the width of the individual nonwoven web section to form a substantially cylindrical tampon blank having an insertion end defined at least in part by the second longitudinal side edge of the individual nonwoven web section and a withdrawal end defined at least in part by the first longitudinal side edge of the individual nonwoven web section; and
   f. a tampon former that transforms the substantially cylindrical tampon blank into the absorbent tampon.

8. Apparatus of claim 7, wherein the individual nonwoven web section feeder comprises a calender.

9. Apparatus of claim 7, wherein the transport section to move the individual nonwoven web section to a winding section comprises a calender.

10. Apparatus of claim 7, wherein the tampon former comprises a tampon forming press.

11. Apparatus of claim 7, wherein the first needlepunching section, the longitudinal edge folding section, and the second needlepunching section are arranged and configured in a single needlepunching unit.

12. Apparatus of claim 7, wherein the second needle density is substantially the same as the first needle density.

13. Apparatus of claim 7, wherein the second needle density is less than the first needle density.

* * * * *